(12) United States Patent
Huang et al.

(10) Patent No.: US 9,354,197 B2
(45) Date of Patent: May 31, 2016

(54) MICROMACHINED OXYGEN SENSOR AND METHOD OF MAKING THE SAME

(71) Applicants: Liji Huang, San Jose, CA (US);
Chih-Chang Chen, Cupertino, CA (US)

(72) Inventors: Liji Huang, San Jose, CA (US);
Chih-Chang Chen, Cupertino, CA (US)

(73) Assignee: Wisenstech Ltd., Santa Clara, CA (US)

( * ) Notice: Subject to any disclaimer, the term of this patent is extended or adjusted under 35 U.S.C. 154(b) by 498 days.

(21) Appl. No.: 13/870,914

(22) Filed: Apr. 25, 2013

(65) Prior Publication Data
US 2014/0318960 A1    Oct. 30, 2014

(51) Int. Cl.
*G01N 27/409* (2006.01)
*G01N 27/407* (2006.01)

(52) U.S. Cl.
CPC .......... *G01N 27/4073* (2013.01); *G01N 27/409* (2013.01); *G01N 27/4071* (2013.01)

(58) Field of Classification Search
CPC ............ G01N 27/4071; G01N 27/409; G01N 27/4062; G01N 27/4067; F01N 2560/025
See application file for complete search history.

(56) References Cited

U.S. PATENT DOCUMENTS

| | | | | |
|---|---|---|---|---|
| 4,668,374 A | * | 5/1987 | Bhagat | G01N 27/4071 204/412 |
| 6,022,754 A | * | 2/2000 | Guillemet | G01N 27/12 438/48 |
| 7,495,300 B2 | * | 2/2009 | Gardner | G01N 27/128 257/252 |

OTHER PUBLICATIONS

Mesh Size Measurement Systems downloaded from the badinotti Group website http://badinotti.com/mesh_measure.html on Sep. 28, 2015.*

* cited by examiner

*Primary Examiner* — Alexander Noguerola

(57) ABSTRACT

The design and manufacture method of an oxygen concentration sensor made with silicon micromachining (a.k.a. MEMS, Micro Electro Mechanical Systems) process for applications of oxygen measurement with fast response time and low power consumption is disclosed in the present invention. The said silicon oxygen concentration sensor operates with an yttrium stabilized zirconia oxide amperometric cell supported on a membrane made of silicon nitride with a heat isolation cavity underneath or a silicon nitride membrane with silicon plug for mechanical strength enforcement.

10 Claims, 6 Drawing Sheets

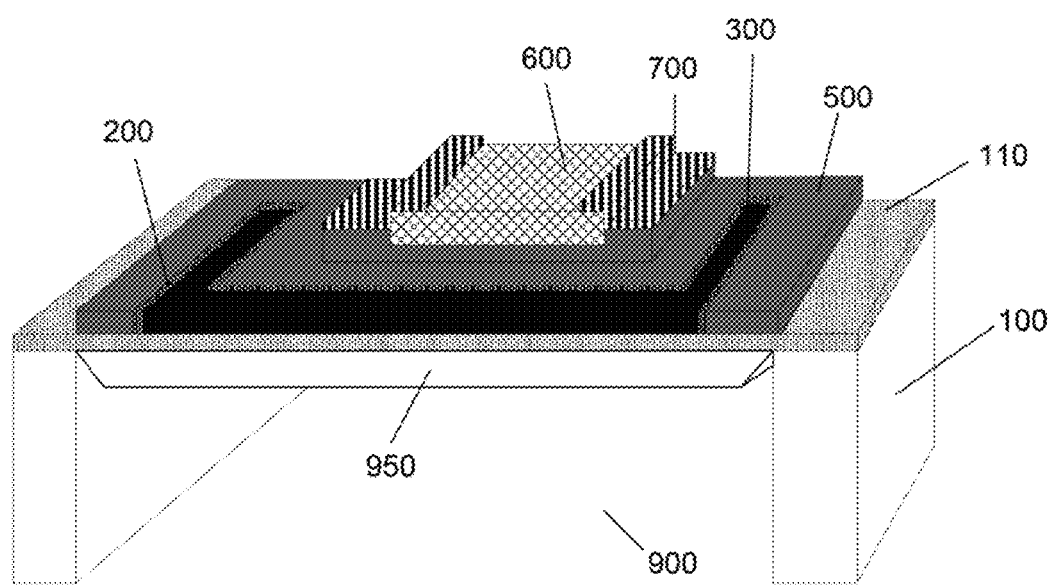
FIG. 1. Schematics of the MEMS oxygen sensor.

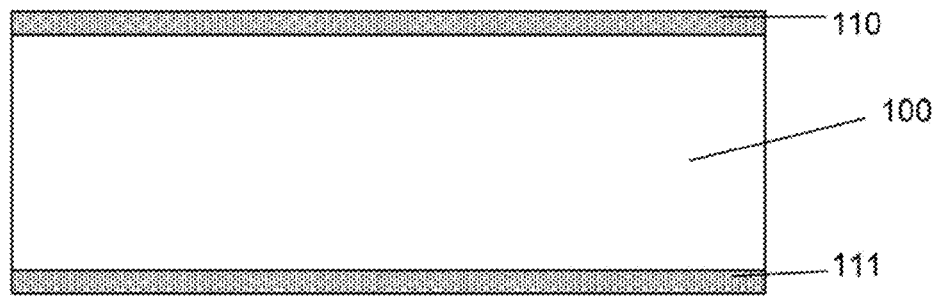
FIG. 2. Bulk silicon with insulation layer.
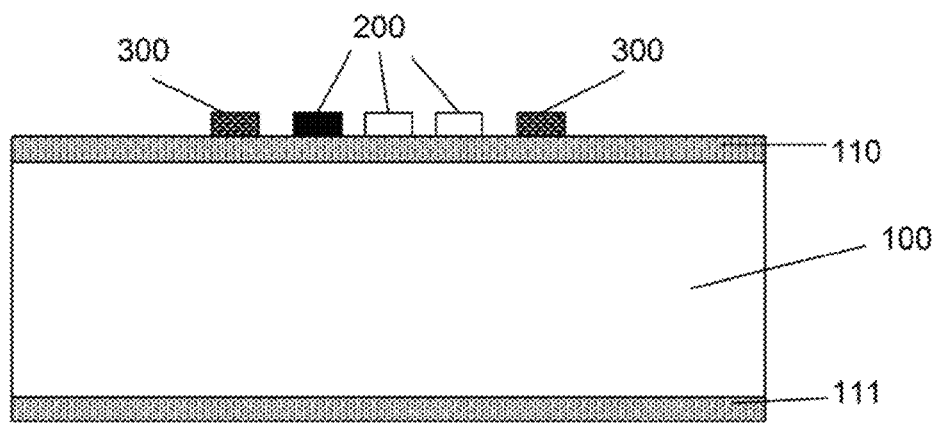
FIG. 3. Deposition of heater and temperature sensor.
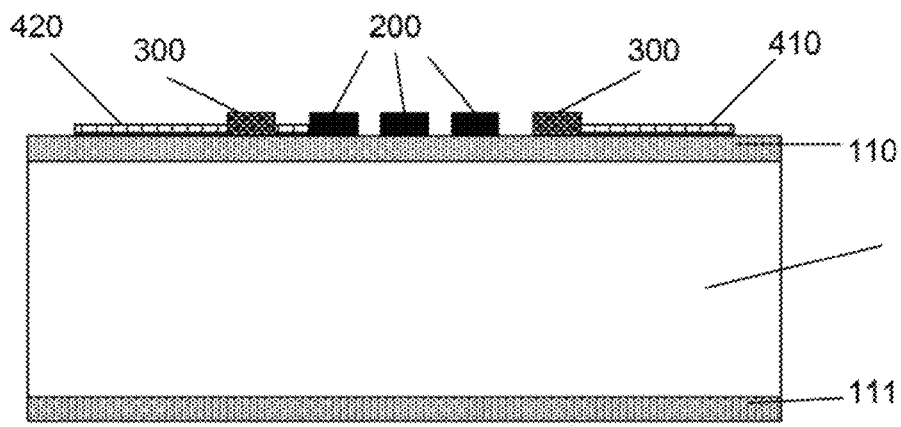
FIG. 4. Formation of insulation for heater.

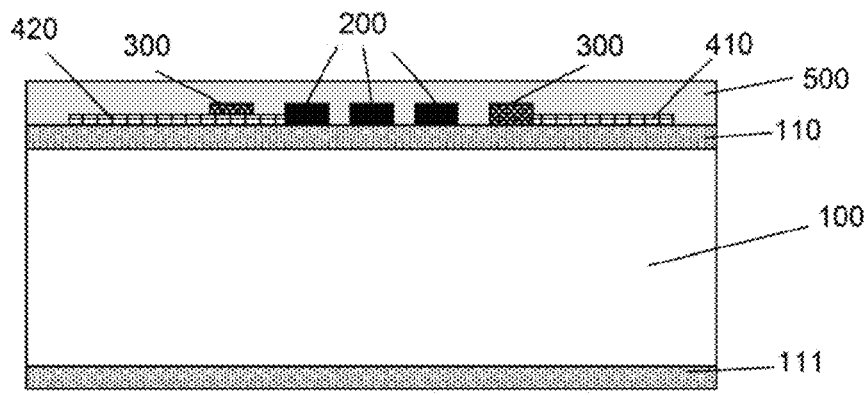
FIG. 5. Form inter-connection and binding pads.
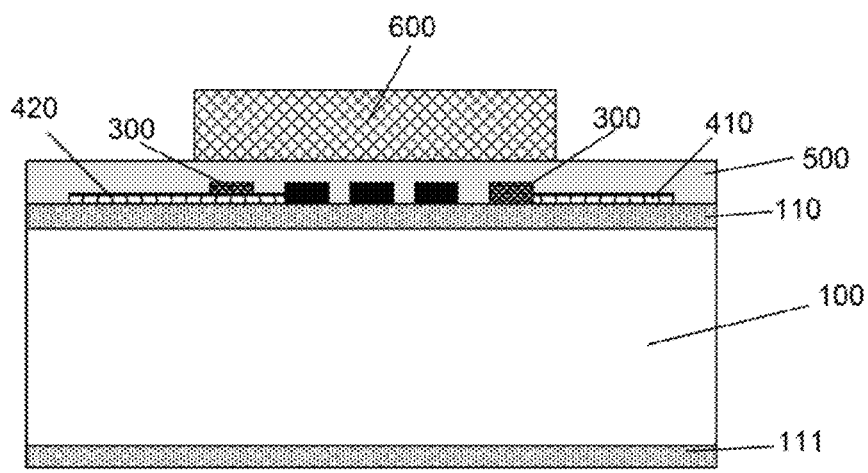
FIG. 6. Form solid electrolyte.
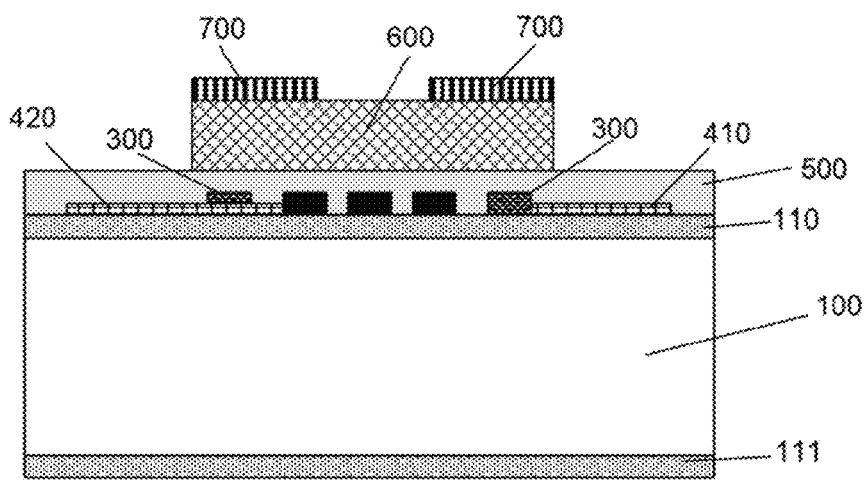
FIG 7. Form electrodes.

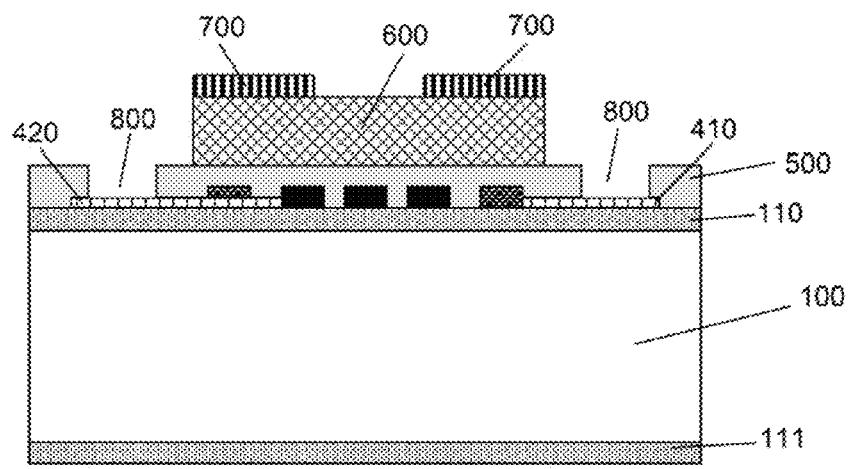
FIG. 8. Form heater/temperature sensor contacts.
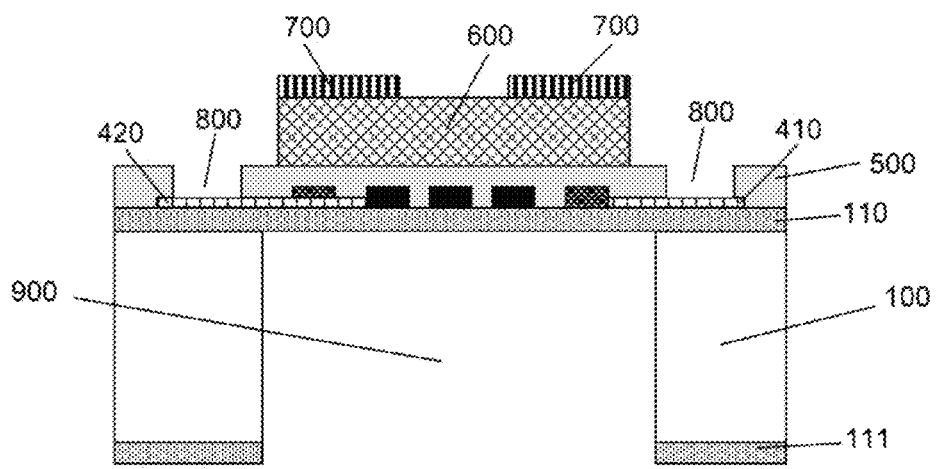
FIG. 9. Form air isolation/cavity.
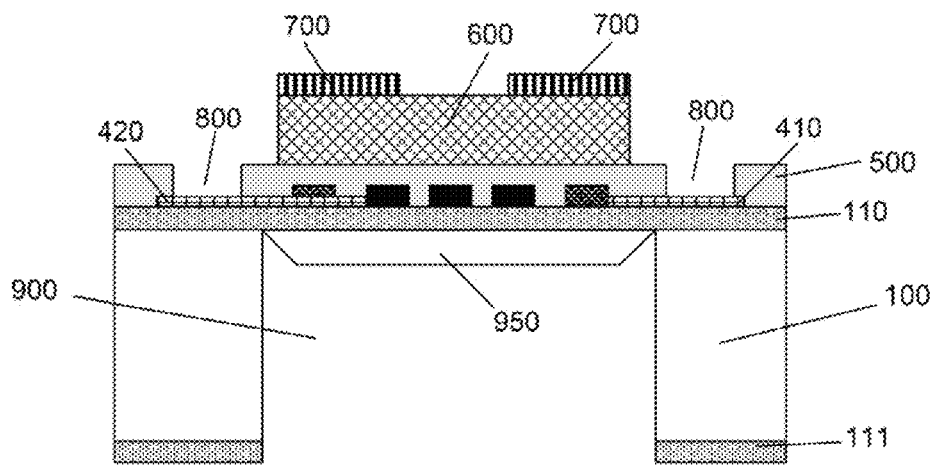
FIG. 9a. Form air isolation/cavity with a silicon plug.

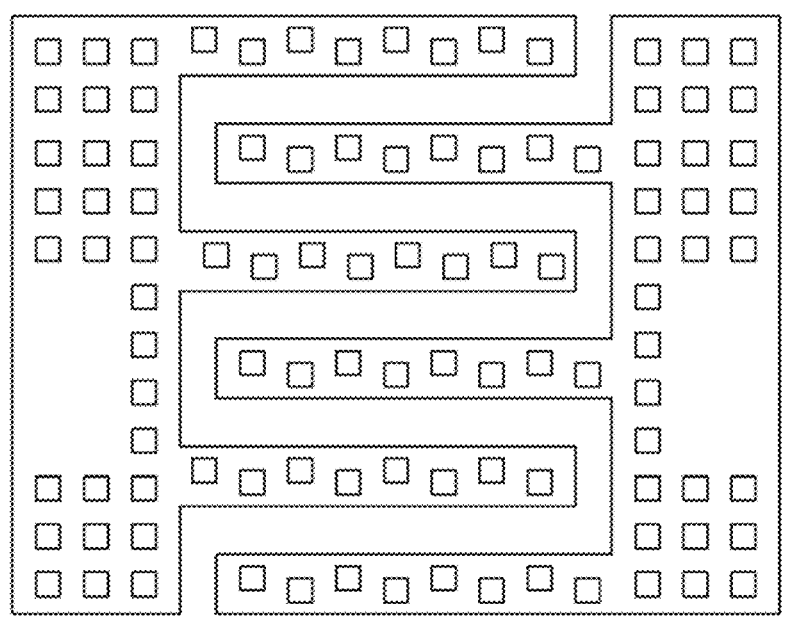
FIG. 10. Electrode pattern.

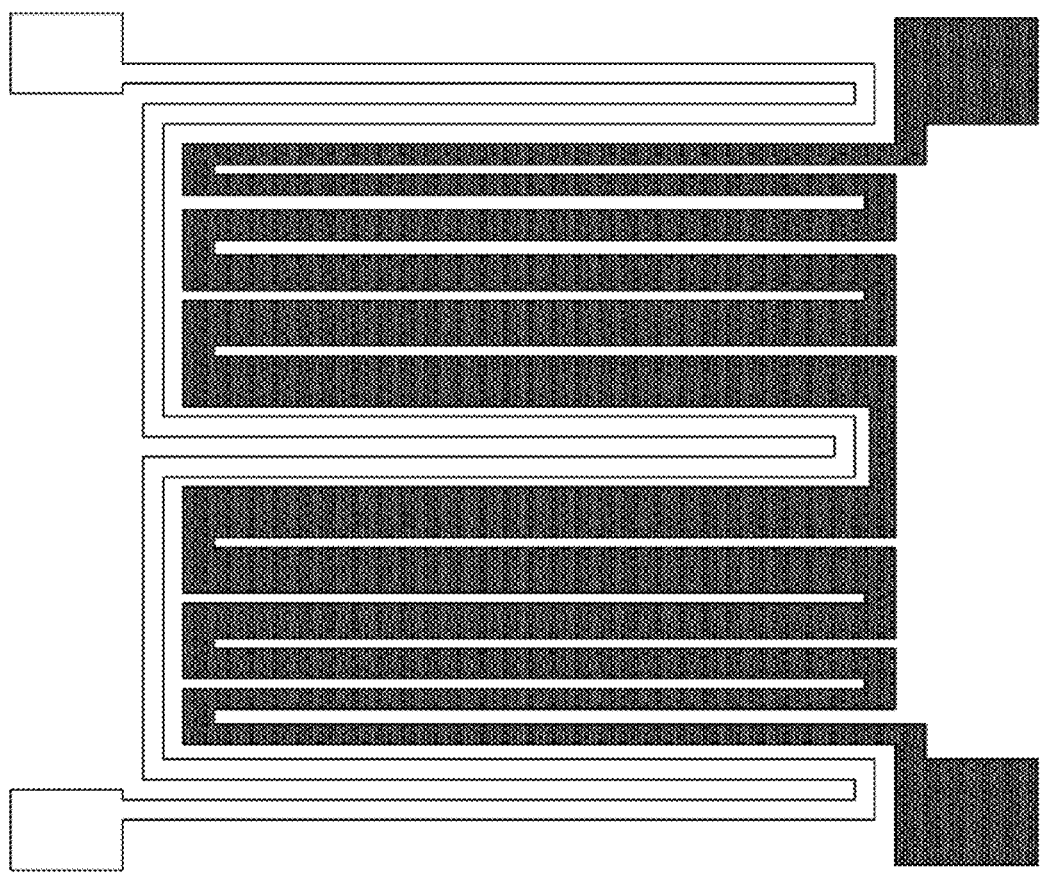
FIG. 11. Heater and temperature sensor.

MICROMACHINED OXYGEN SENSOR AND METHOD OF MAKING THE SAME

We claim the priority to U.S. provisional application Ser. No. 6,164,683, filed on May 2, 2012.

BACKGROUND OF IMF INVENTION

1. Field of the Invention

This invention relates to micromachined silicon sensors or Micro Electro Mechanical Systems (MEMS) gas sensing technology that measures the quality of gases. The present invention also relates to gas concentration sensors of such gases. This invention additionally provides the design and make of a micromachined gas concentration sensor. The present invention specifically relates design and process of making the same for an oxygen concentration sensor using semiconductor solid electrolyte for applications in medical oxygen delivery, automotive fuel efficiency and other industrial emission control equipment.

2. Description of the Related Art

Oxygen concentration sensors have been widely used in gaseous environment such as analytical instrumentation, medical, equipment, automotive exhaust electronic contral unit (ECU), industrial emission control and environment control. However, most of the current oxygen sensors are manufactured with ceramic solid electrolyte or electrochemical cells that suffer a long response time and limited life time. High accuracy oxygen concentration measurement can be achieved using paramagnetic oxygen sensing technology but it is extremely sensitive to vibration and bulk in size in addition to its high cost. For many of the medical applications, response time is critical but the current technologies are yet to offer a practical solution. Oxygen sensor is also a critical component for emission control in an automotive ECU system where the amount of the oxygen at exhaust is used for adjustment of the fuel supply. Such a sensor is made of high temperature ceramic substrate with the yttrium stabilized zirconium oxide as the solid electrolyte and platinum as the electrode in the formality of a Nerost cell. (R. Ramamoorthy, P. K. Dutta, and S. A. Akbar, Oxygen sensors: materials, methods, designs and applications, J. Mater. Sci., 38 (2003) page 4271). The oxygen sensors for ECU system has been mass deployed since mid-1970s and the ECU systems for all cars have been, employed with the oxygen sensors (Topp, B. et aL, Methods for producing oxygen-sensing element, particularly for use with internal combustion engine exhaust emission analysis. U.S. Pat. No. 3,978,006 Aug. 31, 1976; Gold, T. J. et at, Exhaust electrode process for exhaust gas oxygen sensor, U.S. Pat. No. 4,303,490, Dec. 1, 1981; Watson, 1, Exhaust gas oxygen sensor diagnostic method and apparatus, U.S. Pat. No. 8,290,688 Oct. 16, 2012; Mizutani, A. et al., Oxygen sensor, U.S. Pat. No. 6,182,498, Feb. 6, 2001). However, the ceramic based sensor is not only limited to application of low oxygen concentration measurement but also costly for other applications such as motorcycle emission control. The same approaches of the oxygen sensor made on ceramics may take an alternative design utilizing the properties of amperometric characteristics of the zirconia oxide. At high temperature (often over 600° C.), zirconia oxide becomes a conductor to the oxygen ions and current passing through the electrodes shall be proportional to the oxygen concentration. The high temperature requirements of the ceramic oxygen sensors is however a drawback for ambient temperature applications as the local high temperature at the sensor is not desired and power requirement is large. The high temperature requirements also limit the capability of sensor portability as the power shall not be sustainable with most of the available portable energy sources.

Cole et aL (Cole, B. E., Nguyen, Q, and Bonne U., Rugged O2 microsensor, U.S. Pat. No. 5,282,948, Feb. 1, 1994) teaches an oxygen sensor with a silicon substrate and diaphragm made on the substrate containing platinum, silicon nitride and zirconia oxide. This structure is however in tact would be fragile as the limitation for the maximum silicon nitride thickness would be less than 1500 nm and the platinum interlace with silicon and silicon nitride thin film could suffer instability at the elevated temperature that is required for the oxygen sensing reaction for the zirconia oxide. It further reported (Cole, B. E., Uk, E., Schuldt, S., and Bonne, U., Oxygen microsensor development, GRI Tech Report 86/0190, 1986) that such a structure would produce high compressive stress making the sensor unpractical for manufacture. In a later disclosure (Aagard, R. L., Bonne, U. and Cole, B. E., Solid-state oxygen microsensor and thin structure therefor, U.S. Pat. No. 5,389,225, Feb. 14, 1995) by Agards et aL it proposed a solid-state oxygen microsensor which measures the potential difference generated by zirconia oxide based solid electrolyte in a preferably constant temperature gradient. Nonetheless, it did not establish a conventional approach for the control of the temperature gradient and thus making the feasibility of practical manufacture of such is unclear. Further the above disclosed oxygen sensors are most suitable for combustion and emission control applications but not for an oxygen sensor with wide dynamic range and last response time that could be applied for general purpose oxygen concentration measurement.

The said researches and disclosures have yet to produce a general, purpose oxygen sensor except for the $\lambda$ sensor used in the automotive ECU system mostly as an on/off switch. The other oxygen sensors using paramagnetic principle are too costly for the said applications and are best for laboratory use with extremely sensitive to vibration and environmental instabilities.

SUMMARY OF THE INVENTION

In the current invention, one of the embodiments is to form net mesh structure electrodes for the electrolyte cell of oxygen sensor. The net mesh structure electrodes are two comb shape electrodes which are disposed interlaced with each other.

It is therefore desired to provide the design and manufacture process for an oxygen concentration sensor that shall be able to measure the full scale of oxygen concentration and can be easily manufactured. The said oxygen concentration sensor shall have a fast response time such that medical applications will be feasible. It shall be able to operate at a lower temperature with a low power supply compared to the exiting ceramic oxygen sensors. The said oxygen concentration shall further be robust and immune to environmental changes such as vibration. The said oxygen concentration sensor shall also be manufactured at a low cost such that it can be applied for general purpose oxygen measurements.

It is an object of the present invention to design a micro oxygen sensor that can be easily fabricated in volume for the said various applications that require a low cost base. It is then desired to utilize the MEMS manufacture process that is similar to the state-of-the art integrated circuitry manufacture process. The process shall have the character that a higher volume yields a lower cost per the said unit sensor product MEMS manufacture process also enables the identical properties for the said unit sensor product on the same silicon wafer which is important for the final assembly of the said sensor product for the said applications.

It is another object of the present invention to employ the amperometric measurement principle of the solid electrolyte such that the dynamic ranges of the oxygen concentration can be available as desired. For the current solid electrolyte oxygen concentration sensors, the potentiometric approach is utilized. The sensor has one side exposed to the test gas while another side faces to the reference gas. The potential across the sensor is linearly proportional to the logarithm of the ratio of the oxygen concentration at the both side of the sensor. This type of the sensor is not sensitive to high concentration of oxygen but is best used in lean concentration conditions. Therefore the present invention of an amperometric sensing technology based MEMS oxygen sensor in which the electrodes of the designed electrolyte cell shall pump the oxygen from one electrode to another and the resulting current is directly proportional to the oxygen concentration to be measured. This shall result in a much larger dynamic measurement range and the invented MEMS sensor structure shall made the final product easy for manufacture.

It is a further object of the present invention to utilize zirconia oxide or yttrium stabilized zirconia oxide as the solid electrolyte for the oxygen sensing. Other materials such as bismuth oxide and gadolinium oxide can also be used but the yttrium stabilized zirconia is the common and available materials for cost control and easy manufacture purpose. The yttrium stabilized zirconia usually has 8 molecular percentages of yttrium oxide and is made via physical vapor evaporation.

It is yet another object of the present invention to utilize additional metal oxide semiconductors such as titanium oxide for oxygen sensing. The metal oxide semiconductor senses the oxygen concentration due to the change of the electrical resistance of the metal oxide semiconductors. The additional cells of the sensor can he arranged on the said MEMS sensor structure and it shall serve a stand-alone or combined or integrated sensor array that can provide a wide spectrum of the oxygen concentration sensing capability. It shall also provide additional sensing data to reduce the possibility of cross-talking from the presence of other gaseous elements reacting to the zirconia.

It is yet another object of the present invention to fabricate the said sensor via the nanofabrication of the said sensing materials of zirconia oxide or yttrium stabilized zirconia oxide or metal oxide such as titanium oxide so that the thin film sensing materials shall be containing nanostracture for an enhanced surface area for better sensitivity.

It is yet another object of the present invention to integrate a micro-heater beneath the sensing materials to provide a necessary thermal energy for the said measurement principle. The micro-heater shall be made of platinum or tungsten materials or doped polycrystalline silicon. For a better thermal stress management, the micro-heater is preferably made of doped polycrystalline silicon. And the insulation between the micro-heater and the sensing materials shall be provided by silicon nitride or silicon carbide. The insulation layer thickness shall be a few hundreds of nanometers.

It is yet another object of the present invention to integrate a temperature sensor together with the micro-heater such that a precise temperature control of the sensing materials can be achieved. The temperature sensor shall be preferably made of platinum for best stability. And it shall be placed in a feedback circuitry with the micro-heater to control the micro-heater temperature. The best temperature shall be such that a balance between the lifetime and sensitivity of the sensing materials is accessed.

It is yet another object of the present invention to fabricate the said sensor via the MEMS fabrication technology to create a diaphragm structure on silicon or other similar wafer materials such that a cavity beneath the sensing materials could be easily manufactured for maximum thermal isolation and to reduce the power or heat limited by the sensing principle of the said materials. This structure shall further beneficial to the reduction of the response time as the thermal equilibrium shall be much more easier to be established compared to that in a bulk ceramic materials.

It is an additional object to make the membrane structure sturdy to minimize the fragility of the said membrane structure. It is preferably to utilize the MEMS process to form a plug structure beneath the said membrane, i.e. to leave a bulk silicon materials of a thickness of a few micro-meters that shall support the membrane while the cavity beneath the plug shall serve for the thermal isolation functionality.

It is an additional object to employ stat-of-the-art MEMS process technology and thin film deposition technology to manage the stress release and build in the said micro-sensor structure such that to ensure long term reliability of the said sensors. The process of the silicon nitride shall result in a low stress formality and a balance of the metal in form of compressed stress shall be managed.

Other objects, features and advantages of the present invention will become apparent to those skilled in the art through the present disclosures detailed herein wherein like numerals refer to like elements.

BRIEF DESCRIPTIONS OF THE DRAWINGS

FIG. 1 is the schematics of the three dimensional cross-section of the said oxygen concentration sensing built on amperometric sensing principle.

FIG. 2 is showing the process starting steps with a bulk silicon substrate deposition with insulation layer that is also the supporting membrane of the sensor.

FIG. 3 shows the key process step for the making of micro-heater and the control temperature sensor at the same layer of the said oxygen sensor.

FIG. 4 is the key process step of formation of the insulation layer between the micro-heater and the sensing materials of i.e. yttrium stabilized zirconia oxide.

FIG. 5 shows the key process step of forming metallisation or interconnections and the binding pads for connection to control electronics.

FIG. 6 shows the key process step of making the sensing materials or the solid electrolyte of yttrium stabilized zirconia oxide or metal semi-conductor sensing materials.

FIG. 7 shows the key process step of forming the electrodes that pumps the oxygen in between for measurement of the oxygen concentration in the gas environment.

FIG. 8 shows the key process step to open the metal contacts for connection to control electronics.

FIG. 9 shows the key process step of making the thermal isolation cavity underneath the membrane structure.

FIG. 9a shows the key process step of making the thermal isolation cavity underneath the membrane structure with a silicon plug to balance the membrane stress.

FIG. 10 is an example of the electrode that shall be porous or patterned with through holes for efficiency in pumping of oxygen.

FIG. 11 is an example of the micro-heater and temperature sensor beneath the sensing materials that provide required and controllable heat or temperature for the sensing scheme.

DETAILED DESCRIPTION OF THE PREFERRED EMBODIMENTS

The preferred structure of the said micromachined oxygen concentration sensor is illustrated in FIG. 1. The substrate of toe sensor is preferably a silicon single crystal water 100, and the membrane 110 that supports the sensing hierarchy structure. The micro-heater 200 and the temperature sensor 300 shall form a microsystem that provides the required thermal energy for the sensing materials of the solid electrolyte. The sensing materials 600 is preferably yttrium stabilized zirconia oxide and the two electrodes 700 with porous platinum form the amperometric cells for the oxygen concentration sensing at a large dynamic range.

The preferred mieromachining process for making of the said invention starts from the preparation of the isolation cavity process mask and process stop (110 and 111) on the single crystal silicon substrate (100) with a thickness from 0.35 to 0.50 mm. Then the process is followed by the membrane formation for supporting the sensing hierarchy structure and. the said micro-heater heat (200) as shown in FIG. 2, The isolation cavity process mask and process stop (110 and 111) can be made of silicon oxide via thermal oxidization growth in an oven with a thickness of 100 to 300 nni but preferably 150 nm. The grown film 110 is also serving as the membrane and the material is usually selected to be silicon nitride for its mechanical strength. The silicon nitride is preferably made via the low pressure chemical vapor deposition (LPCVD) process at the low stress conditions with a thickness from 800 to 2000 nm but preferably of 1000 to 1200 nm for the management of the total membrane stress and the mechanical robustness of the membrane.

The followed process shown in. FIG. 3 is one of the key processes for the said invention. The micro-heater (200) supplying the required thermal energy for the solid electrolyte is made via the sputtering or electronic beam evaporation of the heater materials that can be tungsten, platinum or doped polycrystalllne silicon. It is preferably to make the micro-heater by tungsten for its heat efficiency and cost but in case the said micromachining process needs to be compatible metal on semiconductor (CMOS) process, doped polycrystalline silicon shall he the best of the choices. The thickness of the said micro-heater can be from 1.00 nm to 300 nm but preferably 200 nm. To enhance the adhesion, a thin layer of a few nanometers of titanium or chromium are made between the silicon nitride and the micro-heater materials. The temperature sensor 300 integrated together with the micro-heater shall provide the accurate measurement of the thermal energy such that the micro-heater temperature can be precisely controlled. The materials of the temperature is preferably platinum with a thickness the same as that for the micro-heater. In case of a CMOS process, doped polycrystalline silicon can be used for the making of the temperature sensor.

The connection of the micro-heater (200) as well as the temperature sensor (300) to the external control interface is illustrated in FIG. 4 and is done via the metallization process (410 and 420). The metallization is preferably made of gold via sputter deposition or electronic beam evaporation due to that thin gold films have small resistance values that shall not have impact on the control electronic circuitry. The preferred thickness of the metallization is 100 to 500 nm but most preferably 200 to 250 nm.

In FIG. 5, isolation layer (500) between the micro-heater, the integrated temperature sensor and the sensing materials is performed via the deposition of the electrically insert but thermally conductive materials on top of the micro-heater (200) and the temperature sensor (300). Preferably process of making the isolation layer is done via the physical vapor sputtering or plasmas enhanced chemical vapor deposition of silicon nitride or silicon carbide with a thickness preferably from 200 to 500 nm but most preferably 350 nm. In preferably cases, silicon nitride is selected due to lower possibility of sharp particles inclusions during silicon carbide preparation that may yield in this process resulting in difficulties in late process.

The sensing material (600) of the solid electrolyte for the said oxygen concentration sensor is preferably made of yttrium stabilized zirconia oxide with yttrium composition of four to eight molecular percentages that had been established for the best sensitivity for the oxygen concentration sensing. This sensing layer is preferably made via a physical vapor deposition process with a thickness of 1000 nm to 4000 nm but preferably 2000 nm directly on the isolation layer (500) as shown in FIG. 6. For the said thickness of the sensing zirconia oxide, the preferably yttrium composition is eight molecular percentages. The preparation of the solid electrolyte could also alternative be made via the electronic beam evaporation of the preformed powder of zirconia oxide with the four to eight molecular percentages of yttrium.

As shown in FIG. 7, the electrodes (700) for the completion of the reactive solid electrolyte cell for the oxygen concentration are made usually via the physical vapor deposition or electronic beam evaporation. As the oxygen ions shall be pumped via one electrode to another, it is critical to make the electrode such that the reaction efficiency can be ensured. To achieve this objective, the electrodes can be made porous via bias of the physical sputtering voltage during foe electrode formation that shall form the paths for the oxygen ions to migrate easily. Alternatively the electrodes could be patterned with regular through holes that shall serve for the oxygen ion migration pathways. The thickness of the electrodes shall be preferably from 100 nm to 400 nm but most preferably 200 nm.

The making of the connection of the micro-heater and the temperature sensor to the external control interface is illustrated in FIG. 8 and is done via the dry ion etching to remove the silicon nitride isolation and yield the openings (800).

FIG, 9 shows the process that removes the bulk silicon material for the thermal isolation cavity (900) beneath the membrane structure. This task is preferably done with the deep reactive ion etching that shall stop automatically when the silicon material is completely removed and the reactive ions reach to the silicon nitride that is the bottom layer of the membrane structure. Alternatively the bulk silicon material can also be removed using the standard potassium hydroxide (KOH) solution or tetramethylammonium hydroxide solution (TMAH).

To enhance the robustness of the said oxygen sensor, such as to increase the resistance to the external pressure applied on the membrane, it is desired to enforce the membrane mechanical strength. In one of the preferred embodiment, a silicon plug (950) as shown in FIG. 9a is made such that the sturdy support remains for the membrane while the cavity beneath the plug shall provide the thermal isolation for a quick thermal balance once the micro-heater is powered with the controlled thermal energy. The silicon plug can be made via the timer stop of the deep reactive ion etching process.

As it has been discussed in the preferred embodiment, the net mesh structure electrodes for the solid electrolyte cell shall be patterned with the through holes for the oxygen ions to migrate for the consistency of the sensors in manufacture. An example of the electrode pattern is illustrated in FIG. 10. The patterned through holes can be any regular geometry while the illustrated one is a square formality. The size of the through holes shall be from half to three square micro-meters but preferably half square micro-meters for the efficiency of the pathways.

The shape of the micro-heater is preferably to be metal-wires in parallel with a wire width of 2 to 8 micro-meters but preferably 5 micrometers as illustrated in FIG. 11. The alternative shape of the heater can be spirals with the non-uniform width in order to ensure a homogeneous heat distribution. The said micro-heater shall have the capability to elevate the said sensing material temperature above its reactive threshold temperature from 350 to 700° C. To precisely control the micro-heater temperature preventing over heat and to minimize the power consumption, the temperature sensor shall be placed close to the micro-heater such that it can provide the feedback for the control of the heater power. The temperature sensor is preferably to be made of platinum for the performance although tungsten or doped polycrystalline silicon can also provide the required information.

While the invention has been described in terms of what are presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

The invention claimed is:

1. A micromachined oxygen sensor with net mesh structure electrodes comprising:
   a silicon substrate;
   a suspending membrane on the silicon substrate with a micromachined cavity underneath;
   a heating element thermistor being connected to a temperature elevation driving circuit and disposed on top of the suspending membrane;
   a temperature sensing thermistor surrounding the heating element thermistor in close proximity and connected to the temperature elevation driving circuit as a temperature measurement feedback to the temperature driving circuit for the heating element thermistor;
   a solid electrolyte formed by a yttrium stabilized zirconia oxide layer and disposed on top of the suspending membrane;
   two net mesh structure electrodes which are formed by a platinum layer and disposed on top of the yttrium stabilized zirconia oxide; wherein the two net mesh structure electrodes are patterned as comb shape electrodes with dense mesh holes; and wherein the two comb shape electrodes are disposed interlaced with each other; and
   two wire bonding pads which are formed by a gold metal layer and patterned on top of the yttrium stabilized zirconia oxide layer.

2. The micromachined oxygen sensor with net mesh structure electrodes of claim 1 wherein
   the suspending membrane is formed of a low stress layer by low pressure chemical vapor deposition (LPCVD) of silicon nitride with a thickness ranged from 6000 Å to 15000 Å.

3. The micromachined oxygen sensor with net mesh structure electrodes of claim 1 wherein
   the heating element thermistor is formed from a material selected from a group consisting of poly silicon, platinum, and tungsten; and wherein the heating element thermistor can elevate the temperature of the yttrium stabilized zirconia oxide layer to between 350 C to 700 C as the operating temperature of the micromachined oxygen sensor.

4. The micromachined oxygen sensor with net mesh structure electrodes of claim 1. wherein
   the thickness of the yttrium stabilized zirconia oxide layer is ranged from 7000 Å to 15000 Å.

5. The micromachined oxygen sensor with net mesh structure electrodes of claim 1 wherein
   a thin titanium layer with a thickness of 50 Å is applied as an adhesion layer between the platinum layer and the yttrium stabilized zirconia oxide layer on the net mesh structure electrodes.

6. The micromachined oxygen sensor with net mesh structure electrodes of claim 1 wherein
   the platinum layer on the net mesh structure electrodes works as a catalyst layer to reduce molecular oxygen into oxygen ions; and the thickness of the platinum layer is ranged from 1000 Å to 2000 Å.

7. The micromachined oxygen sensor with net mesh structure electrodes of claim 6 wherein
   the net mesh structures on the two electrodes can increase the reacting area for molecular oxygen with the catalyst layer of platinum.

8. The micromachined oxygen sensor with net mesh structure electrodes of claim 1 wherein
   the size of the mesh holes on the two net mesh structure electrodes is ranged from 0.5 um to 0.75 um.

9. The micromachined oxygen sensor with net mesh structure electrodes of claim 1 wherein
   the cavity underneath the suspending membrane is formed by a silicon bulk etching from the back side of the silicon substrate.

10. The micromachined oxygen sensor with net mesh structure electrodes of claim 1 wherein
    a passivation layer of LPCVD silicon nitride is deposited between the top surface of the heating element thermistor and the yttrium stabilized zirconia oxide layer; and wherein the thickness of the passivation layer is ranged from 3000 Å to 4000 Å.

* * * * *